US010481056B2

(12) United States Patent
Bugg

(10) Patent No.: US 10,481,056 B2
(45) Date of Patent: Nov. 19, 2019

(54) BOND TEST APPARATUS AND BOND TEST CARTRIDGE WITH INTEGRATED ILLUMINATION SYSTEM

(71) Applicant: NORDSON CORPORATION, Westlake, OH (US)

(72) Inventor: Martin Bugg, Kesgrave (GB)

(73) Assignee: Nordson Corporation, Westlake, OH (US)

(*) Notice: Subject to any disclaimer, the term of this patent is extended or adjusted under 35 U.S.C. 154(b) by 0 days.

(21) Appl. No.: 15/880,556

(22) Filed: Jan. 26, 2018

(65) Prior Publication Data

US 2018/0224363 A1 Aug. 9, 2018

(30) Foreign Application Priority Data

Feb. 9, 2017 (GB) .................................. 1702162.7

(51) Int. Cl.
*G01N 3/00* (2006.01)
*G01N 3/06* (2006.01)
*G01N 19/04* (2006.01)
*G01N 3/24* (2006.01)
*G02B 21/00* (2006.01)
*F21V 8/00* (2006.01)

(52) U.S. Cl.
CPC ............. *G01N 3/068* (2013.01); *G01N 3/24* (2013.01); *G01N 19/04* (2013.01); *G02B 6/0095* (2013.01); *G02B 21/0016* (2013.01)

(58) Field of Classification Search
CPC .......... G01N 3/068; G01N 3/24; G01N 19/04; G02B 6/0095; G02B 21/0016; H01L 2224/859

USPC .......................................................... 73/800
See application file for complete search history.

(56) References Cited

U.S. PATENT DOCUMENTS

| 2,736,792 | A | 2/1956 | Freeland |
| 3,278,738 | A | 10/1966 | Clark |
| 6,078,387 | A | 6/2000 | Sykes |
| 6,310,971 | B1 | 10/2001 | Shiiyama |

(Continued)

FOREIGN PATENT DOCUMENTS

| DE | 10304369 A1 | 8/2004 |
| EP | 2 363 702 A2 | 9/2011 |
| EP | 2 821 770 A1 | 1/2015 |

OTHER PUBLICATIONS

European search report dated Jun. 28, 2018 for EP Application No. 18155153.

*Primary Examiner* — Max H Noori
(74) *Attorney, Agent, or Firm* — Baker & Hostetler LLP

(57) ABSTRACT

A bond test apparatus, and a cartridge and a light guide for the bond test apparatus are disclosed. The bond test apparatus includes a stage for supporting a bond for testing, a test tool having a test tool tip, a drive mechanism for providing relative movement between the stage and the test tool during the bond test, one or more light sources fixed relative to the test tool, a light guide for directing light to the test tool tip. The cartridge includes a test tool having a test tool tip to contact the bond during a bond test, one or more light sources fixed to the test tool, and a light guide for directing light s to the test tool tip. The light guide includes a tubular body to fit around a test tool, and to direct light, using total internal reflection, from a proximal end of the light guide to a distal end of the light guide.

20 Claims, 10 Drawing Sheets

(56) References Cited

U.S. PATENT DOCUMENTS

| | | | |
|---|---|---|---|
| 6,590,670 B1* | 7/2003 | Kato | G01B 11/0608 356/609 |
| 9,170,189 B2* | 10/2015 | Lilley | G01N 3/24 |
| 2008/0074865 A1* | 3/2008 | Lutz | B25B 23/18 362/119 |
| 2008/0257059 A1* | 10/2008 | Peecock | G01N 3/00 73/827 |
| 2012/0123700 A1* | 5/2012 | Tsaur | G01N 19/04 702/41 |
| 2013/0021783 A1 | 1/2013 | Vanko et al. | |
| 2015/0283685 A1* | 10/2015 | Kynast | B25B 23/18 362/119 |
| 2017/0167969 A1* | 6/2017 | Safai | G01N 19/04 |

* cited by examiner

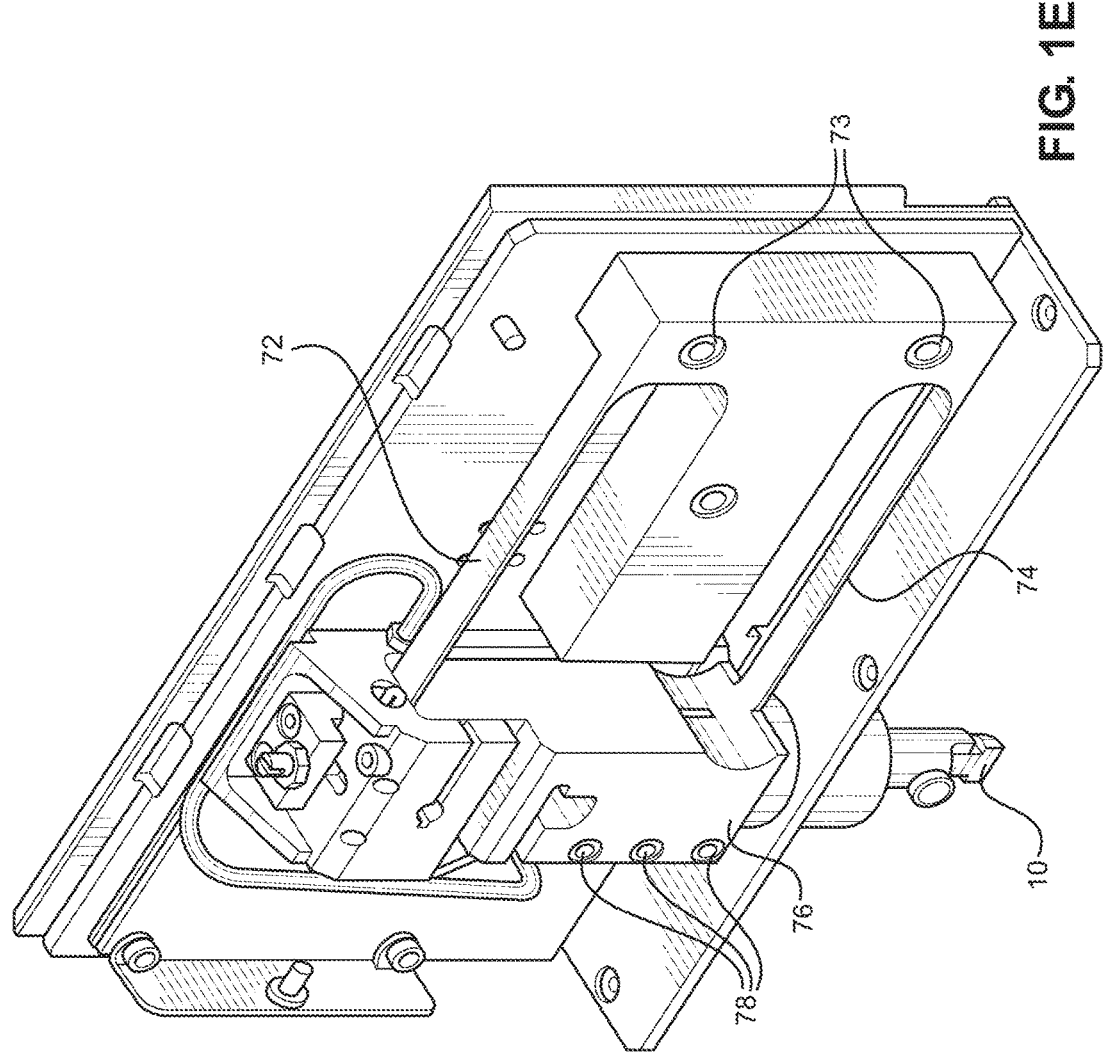

BOND TEST APPARATUS AND BOND TEST CARTRIDGE WITH INTEGRATED ILLUMINATION SYSTEM

CROSS-REFERENCE TO RELATED APPLICATION

This application claims priority to Great Britain Patent Application No. GB 1702162, filed Feb. 9, 2017, the disclosure of which is incorporated by reference in its entirety.

FIELD OF THE INVENTION

The present invention relates to a device for testing the strength of electrical bonds on semiconductor devices. In particular, the invention relates to a system for illuminating a test site in a bond tester.

BACKGROUND

Semiconductor devices are very small, typically from 5 mm×5 mm square to 50 mm×50 mm square, and typically comprise numerous sites for the bonding of electrical conductors to a semiconductor substrate. Each bond consists of a solder ball/bump or copper pillar or wire.

It is necessary to test the bond strength of the bonds, in order to be confident that a particular bonding method is adequate. Because of the very small size of the bonds, tools used to test the bond strength of these bonds must be able to measure very small forces and deflections accurately.

There are several different types of bond tests that are used to test bond strength. For example, shear testing tests the shear strength of a bond by applying a shear force to the side of the bond and shearing the bond off the substrate. Pull testing tests the pull strength of the bond by pulling the bond away from the substrate. In a push test, a force, or load, is applied in the vertical plane directly downward onto a bond.

Machines that perform these tests typically comprise a bond test tool, be it a shear test tool, push test tool or a pull test tool, that can be positioned relative to the bond under test and then either the bond or the tool are moved in order to perform the test, which comprises measuring the force needed to break the bond. Each bond test tool is mounted to a load cell provided with a force transducer and associated electronics.

While there are a variety of different test tools, the part of the machine used to position the test tool and move the test tool or bond during a test may be the same for each test tool. Accordingly, test tools have been designed to be removable from the rest of the machine so that they can be replaced with a different type of test tool or a test tool suitable for a different range of measurements or a different type of bond or test. It may be desirable to use several different test tools on a single substrate under test and so an operator may be required to perform replacement of test tools frequently.

When performing a bond test, it is necessary to illuminate the bond under test with sufficient light to permit accurate pre-alignment and set-up of the test, video recording and visual inspection of the test as it occurs, and subsequent visible inspection of the bond and test tool once it is complete.

Bond test machines are typically fitted with light stalks, which are flexible stalks with a light fitting on a free end. These are fixed to the bond test machine and can be manoeuvred into position to illuminate the test piece. However providing illumination in this way has a number of problems. The light stalks are bulky, and can interference with other elements of bond test machine operation. The position of the light sources inevitably means that there is shadow and inconsistent illumination. The light stalk may be moved accidently and may therefore require frequent re-adjustment. The remote position of the light sources means that illumination may not be optimised for use with miniature test pieces which are now becoming more commonplace (miniature in this context means in the size range of 20 to 100 μm (microns)).

It is an object of the invention to address these problems or at least to provide a useful alternative solution to the problem of illumination in a bond test machine.

SUMMARY OF THE INVENTION

The invention is defined in the appended independent claims. Preferred or advantageous features are set out in the dependent claims.

In one aspect, there is provided a bond test apparatus comprising:
 a stage for supporting a bond for testing;
 a test tool having a test tool tip configured to contact the bond during a bond test;
 a drive mechanism connected between the stage and the test tool and configured to provide relative movement between the stage and the test tool during the bond test;
 one or more light sources fixed relative to the test tool, and
 a light guide fixed relative to the test tool and configured to direct light from the one or more light sources to the test tool tip.

The light guide may guide light from the one or more light sources to the test tool tip by total internal reflection of the light within the light guide. The light may travel through a solid translucent or transparent material of the light guide. Alternatively, or in addition, the light guide may be hollow and the light may reflect off internal reflective surfaces of the light guide. Advantageously, the light guide efficiently directs light from one or more remote light sources to a small area around the test tool tip. This allows low power light sources to be used and can provide for even illumination without shadows.

The light guide may be configured to focus light on the test tool tip. The light guide may comprise a lens configured to illuminate a predetermined area around the test tool tip. The light guide is tapered towards the test tool tip. A tapered portion of the light guide may be configured to direct light towards the test tool tip. Depending on the type of test to be performed and the area that it is desirable to illuminate, different light guides may be used to provide different illumination patterns. The light guide may comprise two or more portions movable relative to one another to provide for variable focussing of the light.

The light guide may be tubular. In particular, the light guide may surround at least a portion of the test tool. The test tool may fit within the light guide. The light guide may be shaped to fit closely around the test tool, so it takes up minimal space around the test tool. The light guide may be shaped to match the shape of the test tool. The light guide may completely surround a circumference of the test tool. This allows for even illumination around the test tool tip, without the test tool tip casting a strong shadow.

The bond test apparatus may comprise a load cell cartridge having a housing, wherein the test tool is fixed to and extends from the load cell cartridge housing, and wherein the one or more light sources are contained in the load cell cartridge housing. The test tool may be part of the load cell cartridge but may be removable from the load cell cartridge.

The light guide may be fixed to the test tool indirectly by being fixed to the load cell cartridge. The light guide may be permanently fixed to the load cell cartridge, but advantageously is removably fixed to the load cell cartridge. Preferably the light guide is fixed to the load cell cartridge by a mechanical interlock. For example, the light guide may be fixed to the load cell cartridge using a bayonet fitting or using a threaded connection. Alternatively, the light guide may be fixed to the load cell cartridge using mechanical fixings such as screws, bolts or rivets.

Alternatively, or in addition, the light guide may be fixed directly to the test tool. The light guide may be permanently or removably fixed to the test tool. The light guide may be fixed to the test tool by a mechanical interlock. For example, the light guide may be fixed to the test tool using a bayonet fitting or using a threaded connection. Alternatively, the light guide may be fixed to the test tool using mechanical fixings such as screws, bolts or rivets.

Advantageously, the light guide can be manually removed from the cartridge or test tool without tools. In a preferred embodiment, the light guide can be twisted on and off of the cartridge or test tool to be manually removed.

The light guide may be formed from a moulded plastics material.

Advantageously, the light guide is formed from an optical grade plastics material. For example, the light guide may be formed from acrylic. One or more surfaces of the light guide may be polished to provide a highly reflective surface. Alternatively, or in addition, one or more surfaces of the light guide may comprise a highly reflective coating. This may reduce unwanted leakage of light from the light guide. Advantageously, an exit surface of the light guide, through which light exits the light guide towards the test tool tip, is polished. This reduces unwanted scattering of the light.

The one or more light sources may be fixed directly or indirectly to the test tool. In a preferred embodiment, the one or more light sources are fixed to the load cell cartridge to which the test tool is also fixed. The one or more light sources may comprise a plurality of different light sources. For example the plurality of light source may comprise light sources of different colour or intensity. The one or more light sources may comprise a plurality of identical light sources.

The one or more light sources may comprise a least one variable intensity light source.

In a preferred embodiment, the one or more light sources comprises at least one light emitting diode (LED). The one or more light sources may comprise a plurality of LEDs arranged around a circumference of the test tool and configured to emit light into the light guide. The LEDs may be mounted on a circuit board in the cartridge. The one or more light sources may be used to provide status indications, such as a fault indication or a ready indication, in addition to illuminating a test area around the test tool tip. For example, the one of more light sources may be configured to flash or have a time varying intensity or a different colour during a test set-up or tool touch-down sensing operation.

The test tool may be any kind of test tool. For example the test tool may be pull test tool comprising a hook or jaws, a shear test tool or a push test tool.

The bond test apparatus may comprise additional lights configured to illuminate a test area.

In another aspect, there is provided a cartridge for a bond test apparatus, the cartridge comprising a test tool having a test tool tip configured to contact the bond during a bond test; one or more light sources fixed relative to the test tool, and a light guide fixed relative to the test tool and configured to direct from the one or more light sources to the test tool tip.

The cartridge may comprise a housing and the test tool may extend beyond the housing. one or more light sources may be LEDs positioned within the housing. The LEDs may be mounted on a circuit board within the housing.

The light guide may be fixed to the housing of the cartridge, advantageously using a mechanical fastening. The light guide may be constructed as described in relation to the first aspect.

In a further aspect there is provided a light guide for a bond test apparatus, the light guide comprising a tubular body configured to fit around a test tool, and configured to direct light, using total internal reflection, from a proximal end of the light guide to a distal end of the light guide.

The distal end of the light guide may be tapered to direct light towards an area surrounding a tip of a test tool. The light guide may comprise an interlock structure at the proximal end configured to mechanically interlock with a corresponding structure on a bond test apparatus. For example the coupling structure may be a bayonet fitting or a screw fitting. The light guide may be formed from an optical grade material. The light guide may be formed from a mouldable plastics material, such as acrylic.

Features described in relation to one aspect may be applied to other aspects. In particular features of the cartridge and light guide described in relation to the bond test apparatus aspect may be applied to the cartridge alone or to the light guide alone.

BRIEF DESCRIPTION OF THE DRAWINGS

Embodiments of the invention will now be described in detail, by way of example only, with reference to the accompanying drawings, in which:

FIG. 1E is a perspective view of the test tool cartridge of the bond test apparatus;

DETAILED DESCRIPTION

Prior Bond Test Apparatus

Figure 1A:
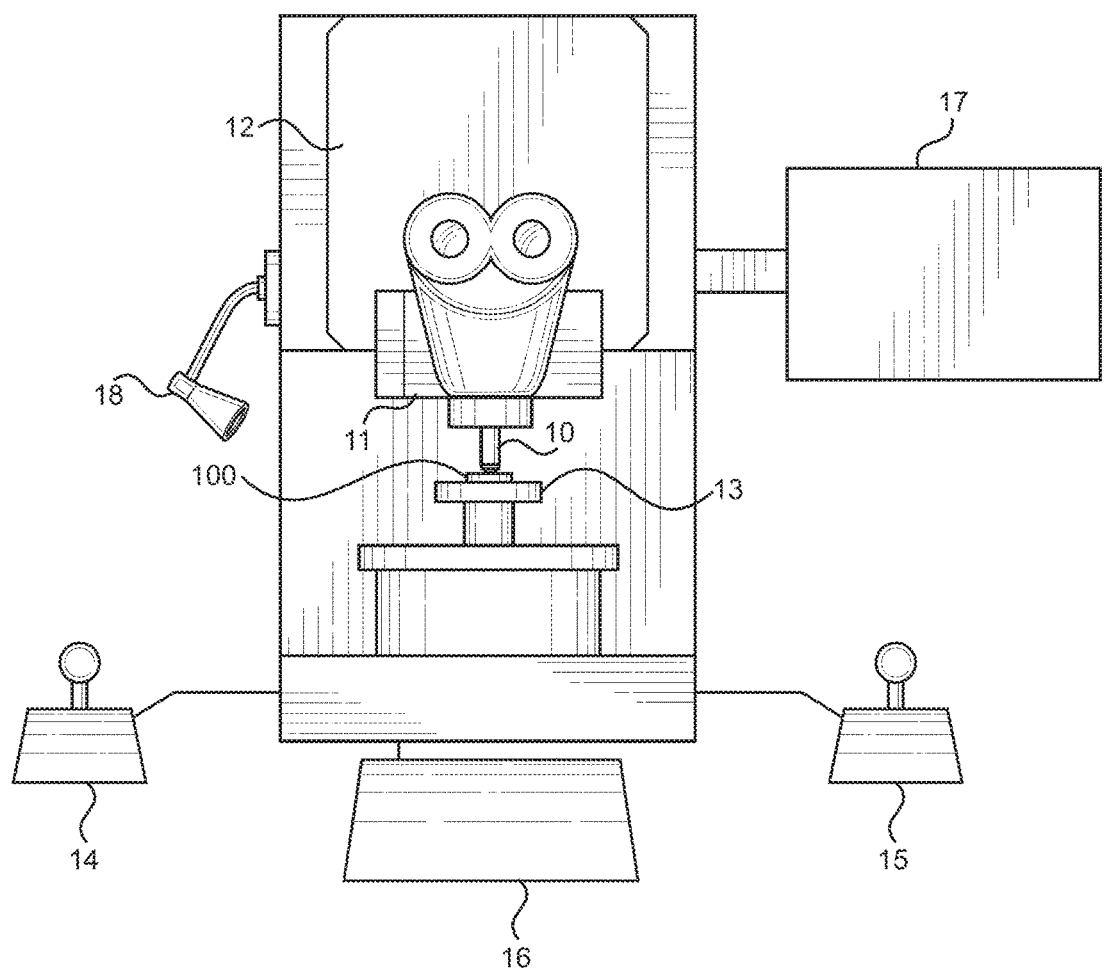
FIG. 1A is a simplified front view of a bond test apparatus that may be used with the present invention.

FIG. 1A is an illustration of a bond testing apparatus in accordance with the present invention. The apparatus comprises a test tool 10 mounted to a test tool cartridge 11, which is itself mounted to the main body of the bond test apparatus 12. Beneath the test tool, the bond test apparatus includes a motorized stage table 13, on which samples or substrates 100 to be tested can be mounted.

The test tool 10, mounted to cartridge 11, can be a shear tool, push tool or a pull tool and can be switched in order to perform different tests. Shear tools are used, for example, for applying a force horizontally across the board to shear a bond off the substrate, and push tools are used, for example, to apply a vertical compression force on a component on the substrate. The force applied by these tools is measured. A pull tool may, for example, have a hook at the bottom of the tool that is used to hook an electrical lead, which is attached between a component and a sample circuit board, with a vertical force being applied to the tool to pull the lead off the board and measure the force required to pull the lead off the board. An example of a suitable shear tool is described in U.S. Pat. No. 6,078,387, the contents of which are incorporated herein by reference. An example of a suitable pull tool is described in U.S. Pat. No. 6,310,971, the contents of which are incorporated herein by reference.

Figure 1B:
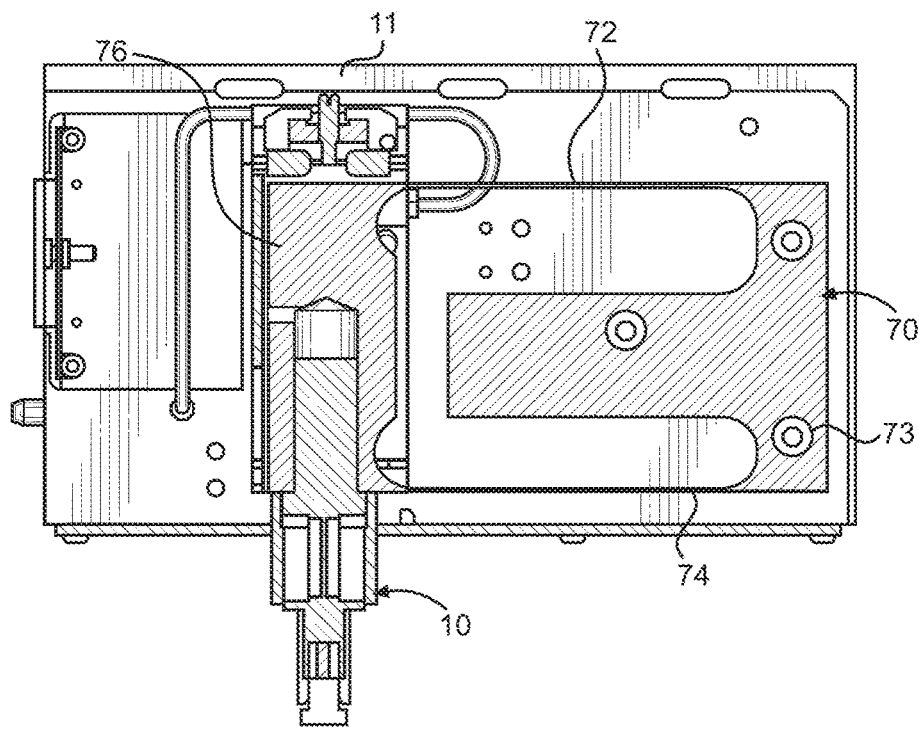
FIG. 1B is a cross-sectional view showing the test tool supported by the tool mounting bracket of the test tool cartridge of the bond test apparatus.
Figure 1C:
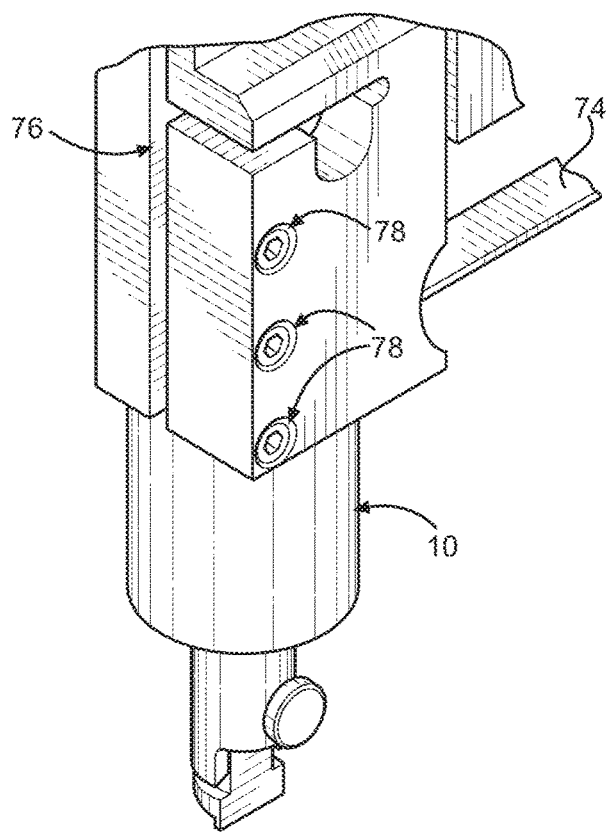
FIG. 1C is a perspective view showing the test tool clamped to the tool mounting bracket.

As shown in FIGS. 1B and 1E, the test tool 10 is typically attached to the cartridge 11 by a tool mount bracket 70 having cantilever arms 72, 74 fixed at one end to the cartridge 11 by screws 73, with the free ends of the arms 72, 74 supporting a clamp 76. As shown in FIG. 1C, the tool 10 is clamped in clamp 76 by means of clamp screw 78. However, any suitable means for attaching a test tool to the cartridge mount plate may be used in a system in accordance with the present invention.

Figure 1D:
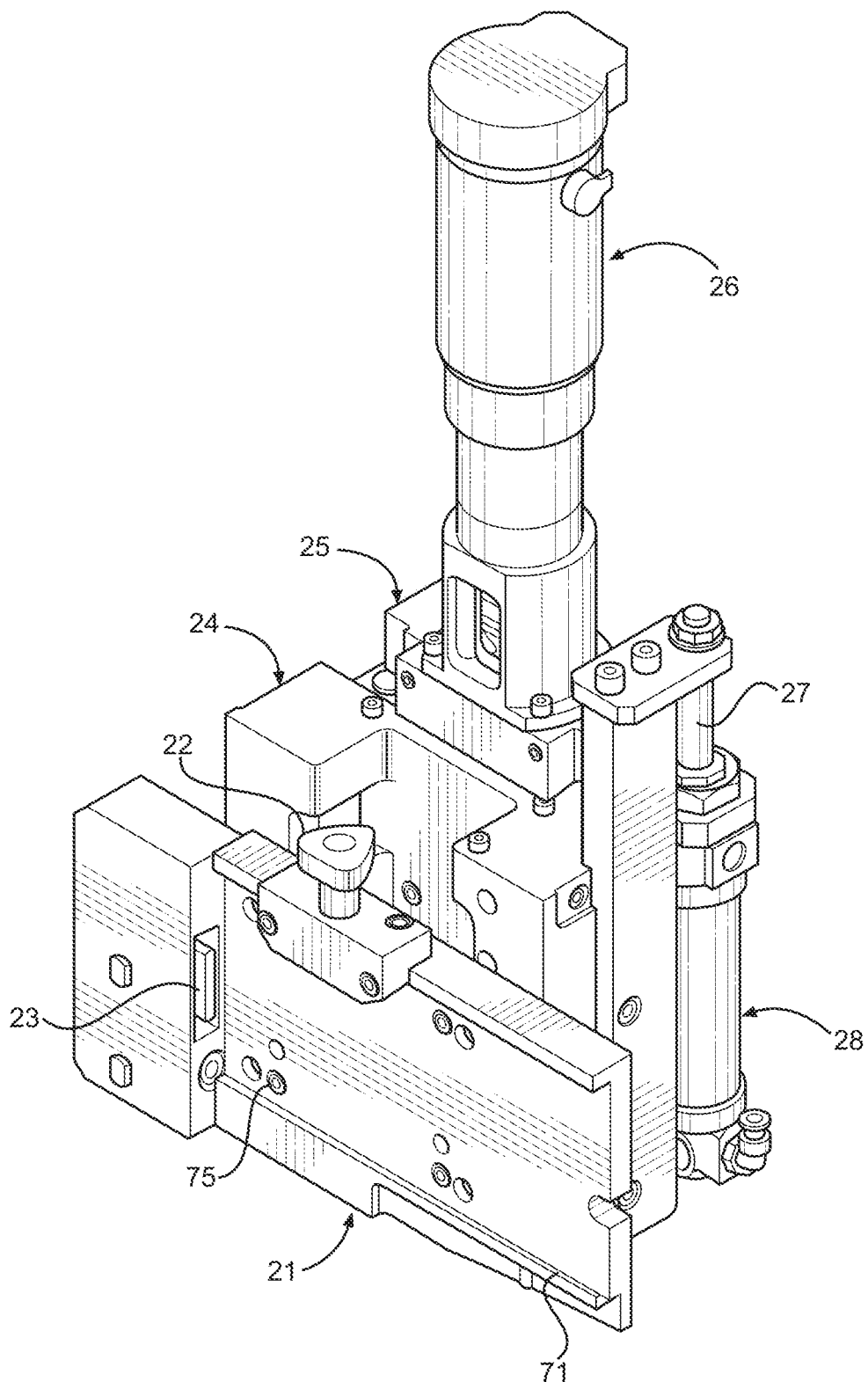
FIG. 1D is a perspective view of a test tool mount and drive portions of the bond test apparatus, including an anti-backlash cylinder.

FIG. 1D shows the retaining channel 71 on the cartridge mount plate 21 into which the test tool cartridge 11 is slid and then secured using one or more screws 22. This design permits different test tool cartridges, having different test tools, to be used with the bond test apparatus, as appropriate for the type of test that the user is conducting. The cartridge mount plate 21 includes a data port 23 that couples with an electrical connector on the test tool cartridge 11 for transferring data from the transducers of cartridge 11 to a PC, such as data representing the force required to shear a solder ball off a substrate or pull a lead off a substrate. An interchangeable test tool cartridge design for a bond test apparatus is well known in the prior art. See for example the Dage 4000 multipurpose bond tester available from Dage Holdings Limited, 25 Faraday Road, Rabans Lane Industrial Area, Aylesbury, Buckinghamshire, United Kingdom.

Figure 1F:
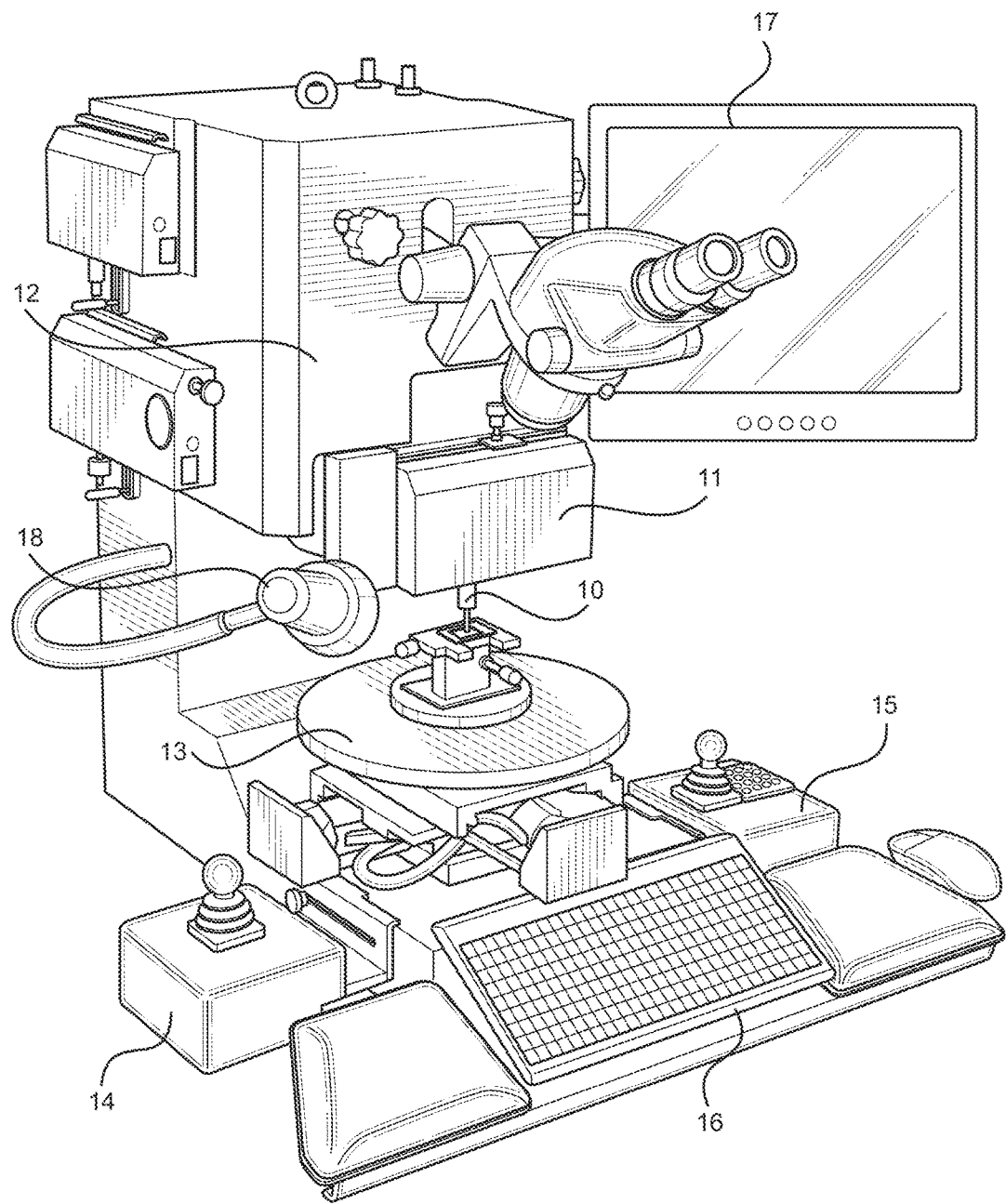
FIG. 1F is a perspective view of the bond test apparatus.

The cartridge 11 is moveable in a z direction normal to the surface of the substrate 100 on the stage table 13. This allows the test tool 10 to be positioned vertically relative to the substrate 100 under test so that it can contact a particular bond during a test. Relative x-y movement between the test tool 10 and the table 13 in a direction parallel to the plane of the substrate 100 is typically achieved by moving the table 13. Movement of the table 13 in x and y is achieved using suitable servo motors or stepper motors, coupled to the table 13 via a lead screw and nut, ball screw and nut, or suitable belt-drive mechanism (not shown), as is also well known in the prior art, such as the Dage 4000 Multipurpose Bond Tester referenced above Also shown in FIGS. 1A and 1F are control devices, comprising two joystick controls 14, 15 to allow for controlling movement of the table 13, and a keyboard 16. A display 17, a light 18 for illuminating the substrate 100 under test, and a microscope, aiding accurate positioning of the test tool 10, are also shown. These features are also all well known in the prior art, such as the Dage 4000 Multipurpose Bond Tester referenced above.

FIG. 1D shows that the mounting plate 21 and its connection to the main body 25. As has been described, the test tool (not shown in FIG. 1D) must be moveable towards and away from a substrate under test. This is achieved by moving the cartridge mount plate 21, to which the test tool 10 is attached, relative to the main body 25 of the device in a direction towards and away from the substrate, herein referred to as the z-axis direction or axial direction. The cartridge mount plate 21 is rigidly coupled to a moving block 24, using screws 75. The moving block 24 is coupled to the main body 25 via a ball screw (or lead screw) and nut and nut block (not shown) that are driven by a servo motor or stepper motor 26.

In order to remove the problem of backlash, an anti-backlash mechanism as described in U.S. Pat. No. 9,170,189 may be included. This mechanism is shown in FIG. 1D, and preferably comprises a pneumatic piston 27 and cylinder 28.

Cartridge Based Illumination Using a Light Guide

Figure 2A:
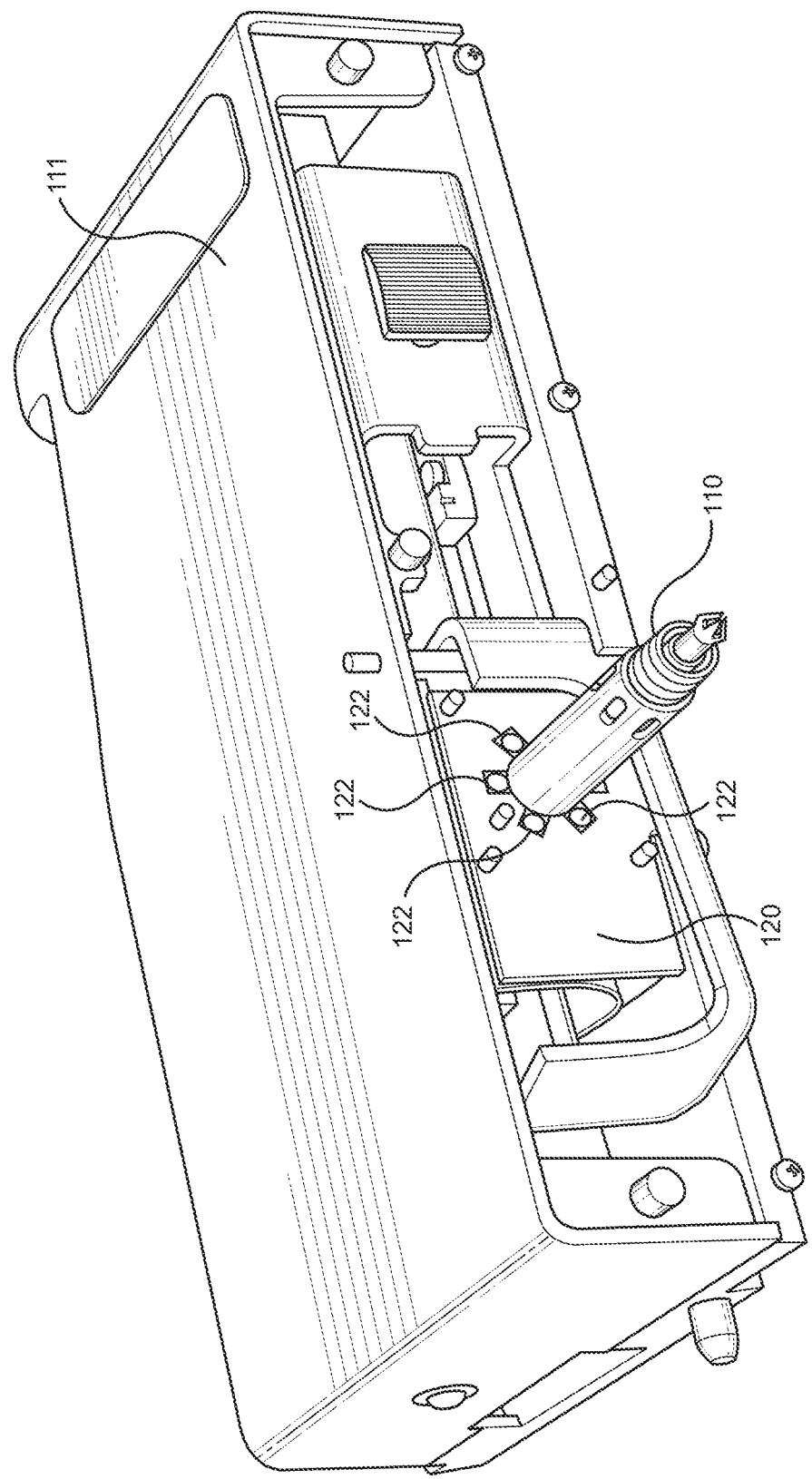
FIG. 2A is an underside perspective view of a cartridge in accordance with the invention, with a light guide removed.

In an embodiment of the invention, in order to improve the illumination of the bond test, both for visual inspection and for video or photographic recording, a plurality of light emitting diodes (LEDs) are provided in the cartridge, positioned around the test tool. FIG. 2A illustrates a cartridge 111 according to one embodiment of the invention comprising a pull test tool 110 fixed to a cartridge mount plate in the manner described with reference to FIGS. 1B to 1E. The test tool 111 has a generally cylindrical shape. Fixed to the cartridge and extending around the test tool 111 is a printed circuit board (PCB) 120 on which a plurality of LEDs 122 are mounted. A portion of the housing of the cartridge is removed in FIG. 2a to show the PCB 120. The LEDs form a ring around the test tool. The LEDS may be controlled to have variable brightness and may have different colours.

In order to use the light from the LEDs more efficiently, and to prevent the test tool casting a shadow over the test site, a light guide is fixed around the test tool to capture light emitted by the LEDs and focus it on the test site, around the tip of the test tool.

Figure 2B:
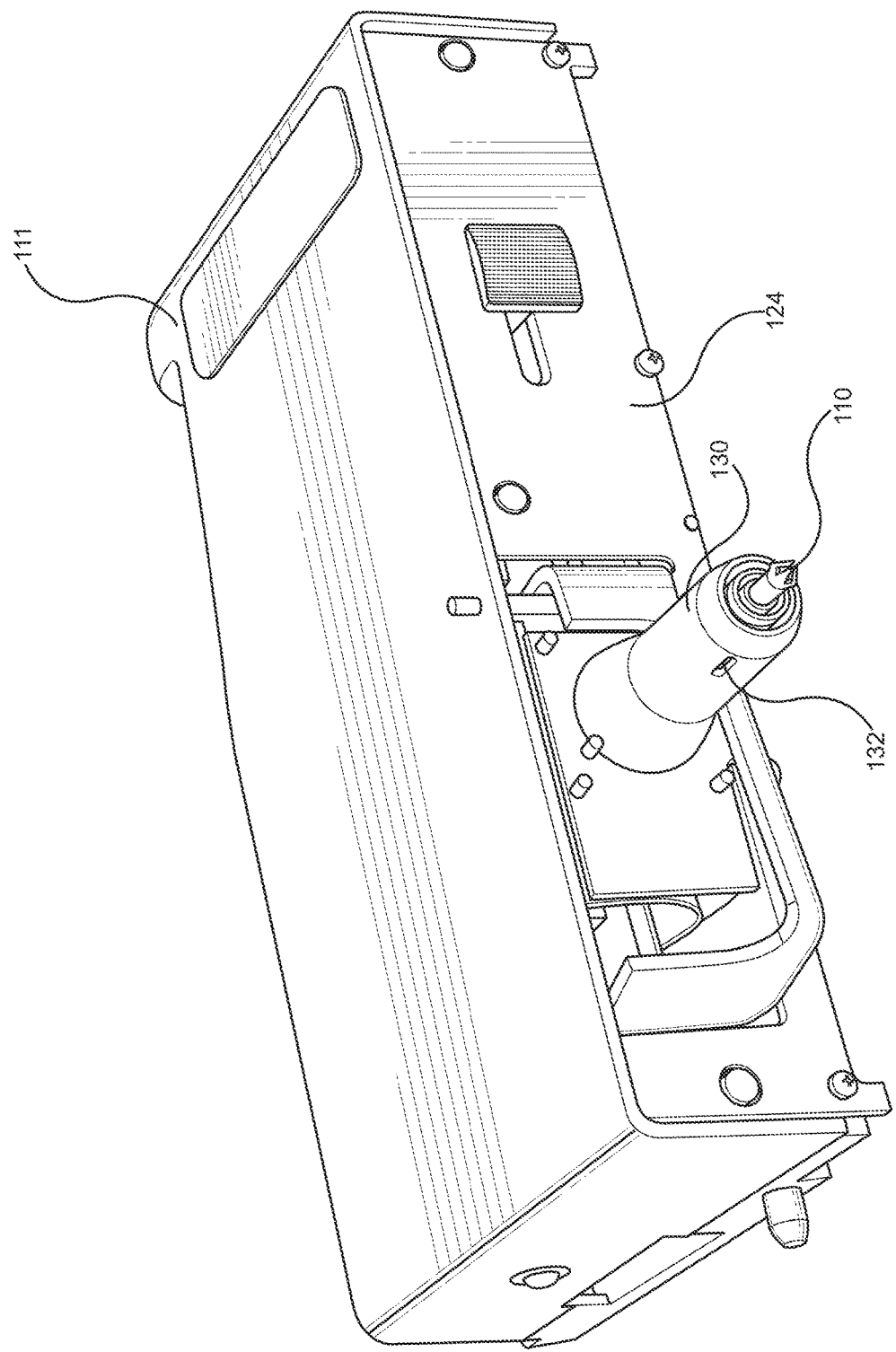
FIG. 2B is an underside perspective view of a cartridge in accordance with the invention, with a light guide attached.

FIG. 2B illustrates the cartridge of FIG. 2A with the bottom plate 124 of the housing fixed over the PCB 120. A tubular light guide 130 is mounted to the cartridge. The light guide 130 has a proximal end positioned adjacent to the LEDs 122 and a distal end close to the test tool tip. The light guide 130 is fixed to the bottom plate 124 of the cartridge housing using a bayonet fitting, as shown in FIG. 3B, so it can be simply placed over the test tool and rotated by hand to lock it in place. The light guide can be removed from the cartridge by performing the reverse operation. In the embodiment shown, the light guide has a pair of slots 132 provided in its sidewall that allow a tool to engage the test tool within the light guide, without having to remove the light guide from the cartridge. This may be desirable for some types of test tool but may not be necessary for other types of test tool.

Light emitted from the LEDs 122 enters the proximal end of the light guide 130 and is prevented from exiting through the side wall of the light guide by total internal reflection. The side wall of the light guide may be provided with a highly reflecting coating to ensure minimal light loss. The light guide has an exit surface 136 at its distal end through which the light escapes. The light guide is tapered at its distal end in order to direct the light at the test tool tip.

The LEDs 122 can have adjustable brightness. This is beneficial as different samples under test may require different brightness illumination. In this embodiment the brightness of the LEDs is controlled using an analogue control of the DC voltage. This differs from the more usual digital modulation of voltage to control LEDs, because modulation might generate noise that would interfere with proper operation of the test tool. The LEDs may also comprise LEDs that emit different colours that may be used to suit different samples under test.

Figure 3A:
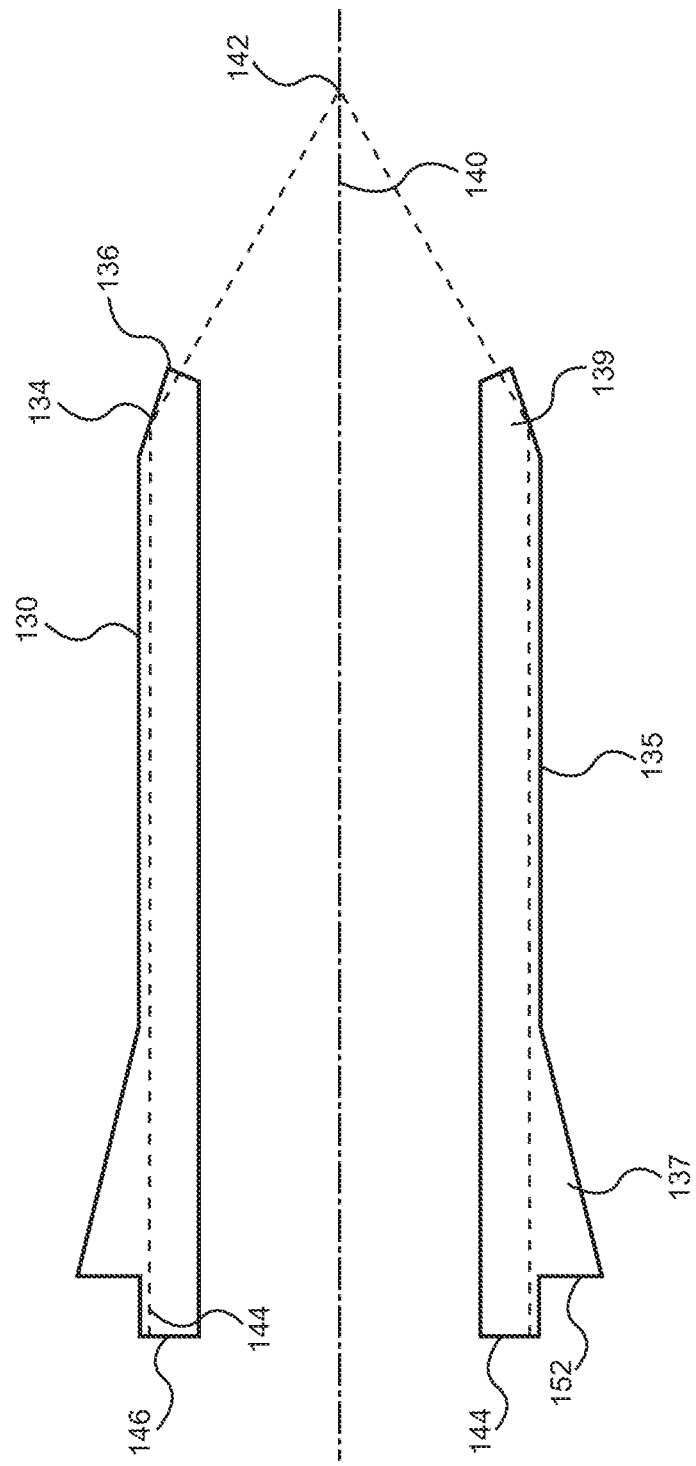
FIG. 3A is a cross section of the light guide of FIG. 2B.
Figure 3B:
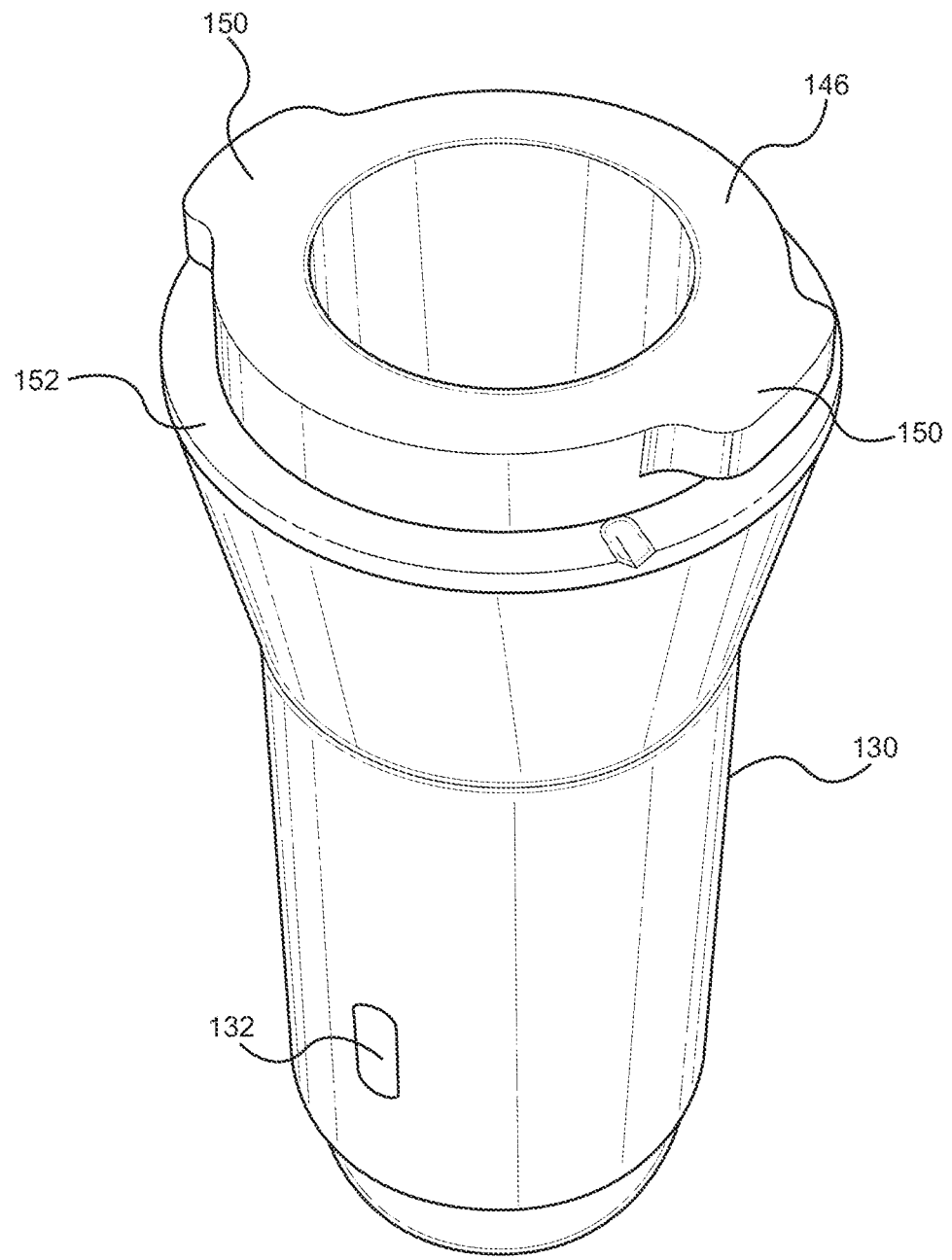
FIG. 3B is a perspective view of the light guide of FIG. 3A.

FIGS. 3A and 3B illustrate the light guide in more detail, removed from the test tool. FIG. 3A is a cross section of the light guide 130. The light guide is generally tubular and is formed from acrylic. Other optical grade materials, such as glass or other optical grade plastics may be used. The light guide has a wall thickness of around 4 mm in a midsection 135 but is wider at the proximal end 137, where it engages the cartridge, and narrower at the distal end 139 where light exits the light guide. The light guide is tapered at the distal end to direct the light towards the test tool tip. The light guide has an internal mirror face 134 at the distal end, which in this example is at an angle of 13° to the longitudinal axis of the light guide.

Lines 144 trace the path of light from the LEDs from entry through proximal surface 146, through the light guide and exit from the light guide through exit surface 136, to a point at the tip of the test tool 142. Line 140 shows the longitudinal axis of the light guide 130.

FIG. 3B is a perspective view of the light guide of FIG. 3A and illustrates the bayonet fitting features 150. The proximal end of the light guide has a pair of wings 150 which extend radially from the main body of the light guide. The wings 150 are received in corresponding slots in the bottom plate 124 of the cartridge housing before being rotated to engage a rear surface of the bottom plate. Surface 152 engages a front surface of the bottom plate.

A pair of slots 138 are also provided in the sidewall of the light guide to allow for easy gripping of the light guide with a tool.

Figure 4:
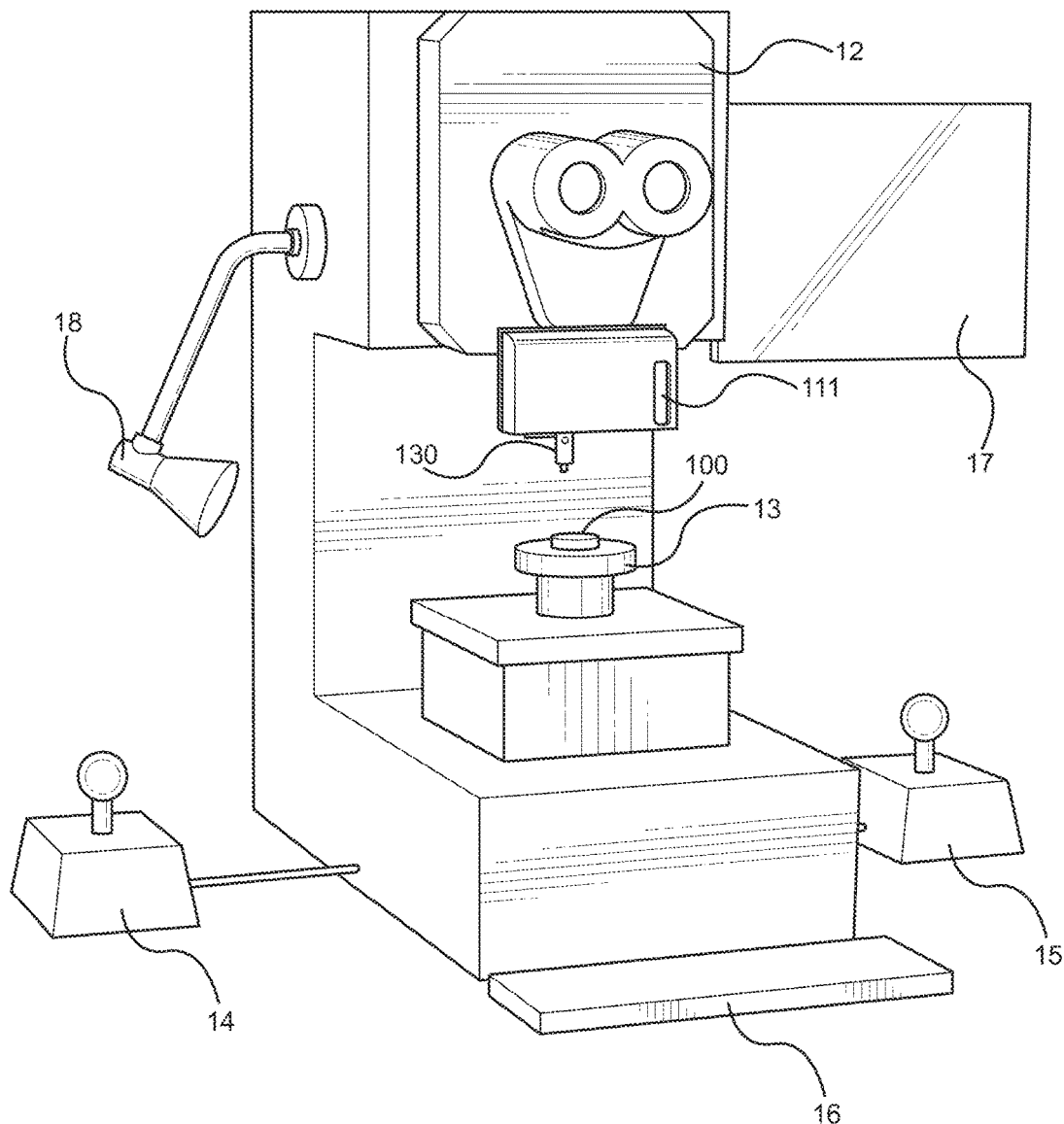
FIG. 4 is a simplified front view of a bond test apparatus including a light guide mounted to the test tool.

FIG. 4 is a schematic illustration of a bond test apparatus, as shown in FIG. 1A, with a light guide 130 positioned around the test tool. The apparatus comprises a test tool within the light guide 130 mounted to a test tool cartridge 111 of the type shown in FIGS. 2A and 2B, which is itself mounted to the main body of the bond test apparatus 12, as described with reference to FIG. 1A. Beneath the test tool, the bond test apparatus includes a motorized stage table 13, on which samples or substrates 100 to be tested can be mounted. Control elements including two joystick controls 14, 15 to allow for controlling movement of the table 13, and a keyboard 16 are shown. A display 17, an additional light 18, and a microscope, aiding accurate positioning of the test tool 10, are also shown.

The provision of a light guide, as described, results in better illumination of the test site in an efficient and controllable manner. The lighting system does not interfere with the test tool operation or with any other aspect of the bond test apparatus, such as microscope viewing. The test tool does not cast a shadow on the test site. Similarly, shadows cast by other components close to the test site are minimised by using the light guide. A light guide can be inexpensively manufactured and easily fitted and removed by a user as necessary. The light guide may also provide some protection for the test tool.

Clearly other designs of light guide are possible and other ways of fixing the light guide to the cartridge or test tool are possible. The arrangement of LEDs and the shape of the light guide may be matched to one another and configured to fit closely around the test tool. The cartridge may allow for different test tools to be mounted to it and so different light guides may be provided to suit different test tools, particularly if the test tools have different dimensions and have a tip at a different location relative to the LEDs. Alternatively, the light guide may be fixed to the test tool during manufacture and provided to the user as a single item.

It is also possible to provide a variable focus light guide by providing lenses within the light guide and allowing them to be moved relative to one another using a sliding or rotating mechanism. However it may be beneficial that there are no moving parts in the light guide as it reduces the possibility of debris falling on the test site. The light stalks of the prior art can cause fine particulate material to be ejected as they are moved, contaminating the test site. A fixed, one piece light guide eliminates that problem.

The light guide described is tubular and extends completely around the test tool. This is advantageous as it provides for uniform illumination. However it is not essential and it may be preferable that the light guide only extends around a portion or portions of the test tool depending on the shape and configuration of the test tool and the requirement for moving parts on the test tool or for access to portions of the test tool during use.

The invention claimed is:

1. A bond test apparatus, comprising:
   a stage for supporting a bond for testing;
   a test tool extending from a proximal end to a distal test tool tip configured to contact the bond during a bond test;
   a drive mechanism connected between the stage and the test tool and configured to provide relative movement between the stage and the test tool during the bond test;
   one or more light sources fixed relative to the test tool; and
   a light guide fixed relative to the test tool, the light guide surrounding at least a portion of a circumference of the test tool, at least partially extending along a longitudinal axis between the proximal end and the distal test tool tip, and being configured to direct light from the one or more light sources to be focused on the distal test tool tip.

2. The bond test apparatus of claim 1, wherein the light guide is tubular.

3. The bond test apparatus of claim 2, wherein the light guide is tapered towards the distal test tool tip to focus the light from the one or more light sources on the distal test tool tip.

4. The bond test apparatus of claim 1, further comprising a load cell cartridge,
   wherein the test tool is fixed to and extends from the load cell cartridge, and
   wherein the one or more light sources are contained in the load cell cartridge.

5. The bond test apparatus of claim 4, wherein the light guide is fixed to the load cell cartridge.

6. The bond test apparatus of claim 5, wherein the light guide is fixed to the load cell cartridge by a mechanical interlock.

7. The bond test apparatus of claim 6, wherein the light guide can be manually removed without tools.

8. The bond test apparatus of claim 7, wherein the light guide can be twisted on and off of the load cell cartridge to be manually removed.

9. The bond test apparatus according to claim 1, wherein the light guide comprises plastic.

10. The bond test apparatus of claim 1, wherein the one or more light sources comprises a plurality of different light sources.

11. The bond test apparatus of claim 1, wherein the one or more light sources comprises a least one variable intensity light source.

12. The bond test apparatus of claim 1, wherein the one or more light sources comprises at least one light emitting diode (LED).

13. The bond test apparatus of claim 1, wherein the light guide is configured to direct the light, using total internal reflection, from a proximal end of the light guide to a distal end of the light guide.

14. The bond test apparatus of claim 1, wherein the light guide is removably coupled to the bond test apparatus while the one or more light sources are fixed to the bond test apparatus.

15. The bond test apparatus of claim 1, wherein a distal end of the light guide is proximal to the distal test tool tip.

16. The bond test apparatus of claim 1, wherein the light guide surrounds an entirety of the circumference of the test tool.

17. A cartridge for a bond test apparatus, the cartridge comprising:

a test tool extending from a proximal end to a distal test tool tip configured to contact the bond during a bond test;

one or more light sources fixed to the test tool; and a light guide fixed relative to the test tool, the light guide surrounding at least a portion of a circumference of the test tool, at least partially extending along a longitudinal axis between the proximal end and the distal test tool tip, and being configured to direct light from the one or more light sources to be focused on the distal test tool tip.

18. The cartridge of claim 17, wherein the light guide is tubular.

19. The cartridge of claim 17, wherein the light guide is tapered towards the distal test tool tip to focus the light from the one or more light sources on the distal test tool tip.

20. The cartridge of claim 17, wherein the light guide surrounds an entirety of the circumference of the test tool.

* * * * *